US006464975B2

United States Patent
Millis

(10) Patent No.: US 6,464,975 B2
(45) Date of Patent: *Oct. 15, 2002

(54) COMPOSITIONS AND METHODS FOR ALTERING CELL MIGRATION

(75) Inventor: Albert J. T. Millis, Schenectady, NY (US)

(73) Assignee: The Research Foundation of State University of New York, Albany, NY (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/459,749

(22) Filed: Dec. 10, 1999

(65) Prior Publication Data

US 2002/0136716 A1 Sep. 26, 2002

Related U.S. Application Data

(60) Provisional application No. 60/111,856, filed on Dec. 11, 1998.

(51) Int. Cl.$^7$ .............................................. A61K 39/395
(52) U.S. Cl. ................................ 424/139.1; 530/387.1; 530/389.2; 424/130.1
(58) Field of Search ........................ 435/7.1, 7.2, 7.21, 435/7.23; 424/130.1, 155.1, 156.1, 174.1, 139.1; 530/387.1, 388.1, 388.8, 388.85, 389.1, 389.2

(56) References Cited

U.S. PATENT DOCUMENTS

5,773,259 A * 6/1998 Kirkpatrick
5,935,798 A * 8/1999 Price et al.
6,060,590 A * 5/2000 Bryant et al.

OTHER PUBLICATIONS

Malinda et al., "Gp38K, a Protein Synthesized by Vascular Smooth Muscle Cells, Stimulates Directional Migration of Human Umbilical Vein Endothelial Cells," Experimental Cell Research 1999, vol. 250, No. 1, 168–173.
Gobe et al., "Clusterin expression and apoptosis in tissue remodeling associated with renal regeneration," Kidney International, vol. 47, 411–420, (1995).
Witte et al., "Platelet activiation releases megakaryocyte––synthesized apolipoprotein J, a highly abundant protein in atheromatous lesions," American Journal of Pathology, Sep. 1993, vol. 143, 763–773.
May, J.F. et al., "The Induction of Atherosclerotic Plaque––Like Mounds in Cultures of Aortic Smooth Muscle Cells" Virchows Arch. B Cell Path. 18:205–211 (1975).
Bostrom, K. et al., "Bone Morphogenetic Protein Expression in Human Atherosclerotic Lesions," J. Clin. Invest. 91: 1800–1809 (1993).

Casscells, Ward, "Migration of Smooth Muscle and Endothelial Cells: Critical Events in Restenosis," Circulation 86:(3) 723–729 (1992).
Wong, P. et al., "Genomic Organization and Expression of the Rat TRPM–2 (Clusterin) Gene, a Gene Implicated in Apoptosis," J. Biol. Chem. 268:(7)5021–5031 (1993).
Collard, M. W. et al., "Biosynthesis and Molecular Cloning of Sulfated Glycoprotein 2 Secreted by Rat Sertoli Cells," Biochemistry 26:3297–3303 (1987).
Jenne, D.E. et al., "Molecular structure and functional characterization of a human complement cytolysis inhibitor found in blood and seminal plasma: Identity to sulfated glycoprotein 2, a constituent of rat testis fluid," Proc. Natl. Acad. Sci. USA 86:7123–7127 (1989).
Schwarts, Stephen M., "Smooth Muscle Migration in Atherosclerosis and Restenosis," J. Clin. Invest. 99:(12)2814–2817 (1997).
Jenne, D.E. et al., "Clusterin: the intriguing guises of a widely expressed glycoprotein," TIBS 17:154–159 (1992).
Blaschukt et al., "Purification and Characterization of a Cell–aggregating Factor (Clusterin), the Major Glycoprotein in Ram Rete Testis Fluid," J. Biol. Chem. 258:(12)7714–7720 (1983).
French, L.E. et al., "Murine clusterin:Molecular Cloning and mRNA Locatization of a Gene Associated with Epithelial Differentiation Processes during Embryogenesis," J. Cell. Biol. 122:(5)1119–1130 (1993).
Diemer, V. et al., "Expression of Porcine Complement Cytolysis Inhibitor mRNA in Cultured Aortic Smooth Muscle Cells," J. Biol. Chem. 267:(8)5257–5264 (1992).
Fritz, I.B. et al., "Novel Action of Carnitine: Inhibition of Aggregation of Dispersed Cells Elicited by Clusterin In Vitro," J. Cell. Physiol. 140:18–28 (1989).
Silkensen, J.R. et al., "Clusterin Promotes the Aggregation and Adhesion of Renal Porcine Epithelial Cells," J. Clin. Invest. 96:2646–2653 (1995).
Millis, A.J.T. et al., "Isolation and characterization of a Mr=38,000 protein from differentiating smooth muscle cells," J. Biol. Chem. 260:(6)3754–3761 ((1985).

(List continued on next page.)

Primary Examiner—Sheela Huff
Assistant Examiner—Larry R. Helms
(74) Attorney, Agent, or Firm—Heslin Rothenberg Farley & Mesiti P.C.; Kathy Smith Dias, Esq.

(57) ABSTRACT

The invention relates generally to compositions useful in altering the migration and/or proliferative activity of cells and to methods of using them. Reagents that can regulate cell migration and reorganization are useful in managing diseases in which cell migration and tissue remodeling play a role, including inhibiting vascular stenosis and restenosis that can result from endothelial injury. Migration-altering compositions include the proteins clusterin and gp38k and fragments thereof which retain the migration-altering activity, peptides derived from the proteins which possess the migration-altering activity, polyclonal, monoclonal and recombinant humanized antibodies directed against the proteins and fragments thereof and anti-sense oligonucleotides capable of binding clusterin and gp38k mRNAs.

3 Claims, No Drawings

OTHER PUBLICATIONS

Millis, A.J.T. et al., "In vitro expression of a 38,000 dalton heparin–binding glycoprotein by morphologically differentiated smooth cells," J. Cell Physiol 127:366–372 (1986).

Shackelton, L.M. et al., "Identification of a 38–kDA heparin–binding glycoprotein (gp38k) in differentiating vascular smooth muscle cells as a member of a group of proteins associated with tissue remodeling," J. Biol. Chem. 270:(22)13076–13083 (1995).

Thomas–Salgar, S.A. et al., "Clusterin expression in differentiating smooth muscle cells," J. Biol. Chem. 269:(27) 17879–17885 (1994).

* cited by examiner

US 6,464,975 B2

COMPOSITIONS AND METHODS FOR ALTERING CELL MIGRATION

CROSS REFERENCE TO RELATED APPLICATION

This application claims the priority of U.S. application Ser. No. 60/111,856, filed Dec. 11, 1998, the entire disclosure of which is incorporated herein by reference.

STATEMENT OF RIGHTS UNDER FEDERALLY-SPONSORED RESEARCH

This invention was made with government support under grant RO1HL40417 awarded by the NHLBI of the National Institutes of Health. The government has certain rights in the invention.

FIELD OF THE INVENTION

The invention relates generally to compositions useful in altering the migration and/or proliferative activity of smooth muscle cells, and to methods of using them, for example, to inhibit vascular stenosis including restenosis following surgical removal of atherosclerotic plaques.

BACKGROUND OF THE INVENTION

Vascular smooth muscle cells (VSMC) of the aorta are situated in an interstitial extracellular matrix which contains glycoproteins, collagens, proteoglycans, and growth factors. VSMC in the normal vessel are in a growth arrested state under the control of homeostatic mechanisms that must be altered to permit cell migration and proliferation, two activities that are the hallmarks of many common diseases such as restenosis following endothelial injury and atherosclerosis. Recent studies have shown that migration of arterial VSMC from the media of the vessel into the intima is an important step in the development of arterial lesions. Clearly, reagents that can regulate VSMC migration and reorganization will be useful in managing the restenosis that can result from endothelial injury, for example, as the result of procedures such as angioplasty and endarterectomy.

Percutaneous transluminal coronary angioplasty (PCTA) is widely used as the primary treatment modality in many patients with coronary artery disease. Two problems associated with the procedure are restenosis after angioplasty or where the patient is not a candidate for angioplasty. Administration of compositions which can alter cell migration and reorganization in conjunction with angioplasty can reduce the possibility of restenosis. When reducing lumen obstruction by angioplasty is not an option, altering cell behavior, specifically the processes related to angiogenesis, may provide an alternative treatment for overcoming myocardial ischemia in patients with coronary artery disease.

SUMMARY OF THE INVENTION

The present invention relates to compositions for altering the migration and proliferative activity of smooth muscle cells. Migration-altering compositions include the proteins clusterin and gp38k, fragments thereof which retain the migration-altering activity, peptides derived from the proteins which possess the migration-altering activity, and polyclonal, monoclonal and recombinant humanized antibodies directed against the proteins and peptides and fragments thereof.

In one aspect, the invention relates to peptides and analogs thereof containing functionally equivalent amino acids that are derived from proteins intimately involved in vascular smooth muscle cell migration and reorganization. These peptides may be chemically synthesized, obtained by limited proteolytic digestion of the proteins or produced by recombinant technology.

In yet another aspect, the invention relates to polyclonal, monoclonal, and recombinant humanized antibodies, and fragments thereof, directed against proteins essential for migration, proliferation and tube formation of vascular endothelial cells.

In still another aspect, the invention relates to a DNA sequence which codes for an RNA that is complementary to and capable of binding to a transcribed sequence of clusterin.

In yet another aspect, the invention relates to a DNA sequence which codes for an RNA that is complementary to and capable of binding to a transcribed sequence of gp38k.

In a related aspect, the invention relates to a method of altering cell migration by contacting said cells with a migration-altering protein, polypeptide or polynucleotide composition derived from clusterin or gp38k.

In another related aspect, the invention relates to therapeutic methods involving surgical or intravenous introduction of such compositions directed to certain target cell populations, such as smooth muscle cells or cancer cells, requiring modulation to ameliorate a disease state, particularly for treating conditions such as stenosis following vascular trauma or disease, atheroclerosis, or cancer.

In another aspect, the invention relates to a method for inhibiting restenosis by preventing translation of the specific nucleic acid sequences which encode clusterin and gp38k. A nucleotide sequence which is complementary to and capable of binding to an mRNA which codes for these proteins can be used to reduce the amount of clusterin and gp38k constitutively produced in response to injury. Application of an antisense molecule of the type described may be administered prior to or contemporaneously with PCTA at the site where atherosclerotic plaques are to be removed.

In a closely related aspect, the invention relates to a method of reducing restenosis in a patient following angioplasty or endarterectomy comprising administering to a patient a therapeutically effective amount of an antibody directed against a migration-altering composition. The antibody is an anti-clusterin antibody or an anti-gp38k antibody, and it inhibits the chemotactic or mitotic activity of the migration-altering composition.

In yet another aspect, the invention relates to the use of migration-altering compositions as anti-tumor agents. Inhibition of angiogenesis deprives tumor cells of needed blood supply and leads to tumor cell death and diminution of the tumor.

In another aspect, when it is desirable to increase the vasculature, thereby providing a blood supply, local application of a migration altering composition can initiate the smooth muscle cell processes involved in angiogenesis and vasculogenesis.

DETAILED DESCRIPTION OF THE INVENTION

In the description that follows certain conventions will be followed as regards the usage of terminology. The term "migration" of vascular smooth muscle cells (VSMC) means movement of these cells in vivo from the medial layers of a vessel into the intima, such as may also be studied in vitro by following the motion of a cell from one location to another (e.g. counting of smooth muscle cell migration out of a defined area in the tissue culture over time.) Migration of cells other than VSMC can also be measured in vitro.

The term "migration-altering composition" encompasses two types of compounds: those which are capable of inhibiting the migration of cells as well as those compositions which induce migration and proliferation. Such compositions include but are not limited to: clusterin and fragments thereof, gp38k and fragments thereof, peptides derived from clusterin; peptides derived from gp38k; polyclonal and monoclonal antibodies capable of binding clusterin and fragments thereof, polyclonal and monoclonal antibodies capable of binding gp38k and fragments thereof, recombinant humanized versions of anti-clusterin and anti-gp38k antibodies; and oligonucleotides, for example, antisense sequences of the genes which encode clusterin and gp38k.

The term "peptide", as it is commonly understood in the art, refers to a molecule of less than 10 kilodaltons (kDa) which is a polyamide of α-aminoacids. For purposes of practicing the present invention, peptides may be obtained by proteolytic digestion of the protein of interest, chemically synthesized or produced by recombinant technology.

The term "functionally equivalent" is used to describe an amino acid that when inserted into an amino acid sequence for a functional protein or peptide does not change the activity of the protein or peptide. Commonly, basic residues can be replaced by other basic residues, for example, arginine can be replaced by lysine or histidine and vice versa without the functional integrity of the molecule being compromised. Similarly, acidic residues can be substituted for acidic residues for example, glutamic acid for aspartic acid; neutral residues can be replaced with neutral residues, for example, glycine, alanine, valine, leucine or isoleucine can be substituted for each other.

The term "a therapeutically effective amount" refers to that amount of a migration-altering composition sufficient to induce or inhibit cell migration depending on the disease or condition being treated. The magnitude of a prophylactic or therapeutic dose of a migration-altering composition in the management of disease will vary with the severity of the condition to be treated and the route of administration. The dose and perhaps the dose frequency typically varies according to the age, body weight and response of the individual patient. Further, it is noted that the clinician or treating physician will know how and when to interrupt, adjust, or terminate therapy in conjunction with individual patient response.

Clusterin and gp38k are two proteins essential for VSMC migration and reorganization. The present invention relates to protein, polypeptide or polynucleotide compositions whose sequence is derived from clusterin and gp38k and methods of altering migration and proliferation of smooth muscle cells using these compositions. For example, peptides derived from these molecules, antibodies directed against them, and fragments thereof, function to inhibit cell migration and differentiation, thereby providing the means to inhibit processes normally involved in stenosis. Conversely, other migration-altering compositions, for example, the proteins themselves and fragments thereof can be used to initiate tissue remodeling by VSMC, wound healing and angiogenesis.

Clusterin

Clusterin is an 80 kDA heterodimeric glycoprotein derived from a 60 kDA polypeptide precursor via N-linked glycosylation, subsequently cleaved into a disulfide linked heterodimer, and secreted. It has been identified in a broad range of tissues where it has been referred to as complement cytolysis inhibitor, sulfated glycoprotein-2, testosterone repressed prostate message-2, SP-40,40, and apoJ. It has been generally localized to epithelial cells and specifically in areas of tissue remodeling. However, in situ hybridization of vascular tissue samples indicates that its expression is regionally restricted to myocytes in the heart and to smooth muscle cells in some of the large and medium size arteries. The specific function of clusterin has been heretofore unknown.

A significant and substantial increase in the synthesis and secretion of clusterin occurs in cultured vascular smooth muscle cells (VSMC) during the time when the culture modulates from a proliferating monolayer morphology to nodular cell culture morphology. The in vitro process of nodule formation appears to model some aspects of in vivo vascular remodeling that occurs in response to injury. For example, following vessel injury, smooth muscle cell adhesion to the medial extracellular matrix is modified as the medial smooth muscle cells migrate into the neointima where they proliferate and undergo phenotypic modification. Subsequently those cells cease proliferation and migration and appear to redifferentiate. In culture, VSMC undergo analogous morphological changes in which a proliferating monolayer of VSMC reorganize to form multicellular nodules. In vitro nodule formation is facilitated by the presence of a well developed extracellular matrix, associated with increased expression of SM α-actin, and is accompanied by production of clusterin.

To demonstrate the role of clusterin in cellular processes, the following materials and methods were employed.

Cells and Stable Transfection

Porcine vascular smooth muscle cell cultures (VSMC) derived from thoracic aorta explants were subcultivated in medium Ml99 (Life Technologies, Inc., Grand Island, N.Y.) supplemented with 10% fetal bovine serum (FBS)(Hyclone, Logan, Utah) as previously described. For transfection, VSMC were plated at $1-2\times10^4$ cells/cm$^2$ in a 90 mm dish containing medium M199 supplemented with 10% FBS and grown to confluency. VSMC were co-transfected with pEMSV scribe α2 containing murine clusterin in antisense orientation and pRSV-NEO at a ratio of 2:1 using calcium phosphate coprecipitation and a mammalian transfection kit (Stratagene, La Jolla, Calif.). Murine clusterin was inserted into a unique EcoRI restriction site, between the Maloney sarcoma virus Long Terminal Repeat (LTR) and SV40 PolyA(+) sequence, which are flanked by T3 and T7 promoters, respectively. VSMC were exposed to the precipitate in the presence of M199 with 10% FBS for 12 hours, washed with Hank's balanced saline solution to remove CaPO$_4$, and allowed to recover in the presence of M199 with 10% FBS for 4 days before being split 1:3 for selection. VSMC were allowed to attach 24 hours before selection 500 μg/ml of G418 (Life Technologies, Grand Island, N.Y.) for 10 days. Neomysin-resistant colonies were visible microscopically and allowed to grow to >50 cells before isolation by use of cloning rings. Stable transfectants were analyzed for the expression of murine clusterin antisense sequences using RT-PCR.

Conditioned Media

Conditioned media were produced from non-cloned VSMC or from clone SM-CLU18AS as previously described. Briefly nodular cultures were washed three times in Hank's buffered saline solution and incubated in M199 without serum for 24 hours. Conditioned medium was collected in 1 mM phenylmethylsulfonyl fluoride and 1% aprotinin, centrifuged to remove debris and either used directly or concentrated using a Centricon-30 (Amicon, Beverly, Mass.) filtration system.

Reconstituted Matrix

Collagen-gel substrates were formed in six-well cluster dishes (Falcon Plastics, Beckton-Dickinson) coated with a 420 µl solution consisting of 360 µl cold rat tail collagen I (Collaborative Biomedical Products, Bedford, Mass.), 42 µl cold 0.1N NaOH, and 42 µl cold 10× phosphate-buffered saline, with final pH adjusted to 7.4 using 0.1 N NaOH. Gels were formed by incubation at 37° C. for >30 min. Matrigel substrates were formed by thawing Matrigel at 4° C. and diluting 1:1 with serum free M199. Precooled dishes were coated with 50 ul/cm$^2$ diluted Matrigel and incubated at 37° C. for >45 min.

Nodule Quantification

VSMC were harvested and mixed with an equal volume of 40 µg/ml soybean trypsin inhibitor (Sigma, St. Louis, Mo.), centrifuged, resuspended in 199 containing 10% FBS, and plated onto the matrix at 5.5×10$^4$ cells/cm$^2$ and incubated for the times indicated with each figure. Images of non-fixed cultures were obtained using a Videoscope imaging camera attached to an Olympus CK2 inverted microscope fitted with a 4× objective. Images were then processed using Metamorph imaging software running on an IBM-PC (Universal Imaging Corporation, West Chester, Pa.) and quantified using Excel (Microsoft Corporation).

Immunoblot Analysis of Clusterin In Culture Medium

VSMC or clone SM-CLU18AS cells were seeded at density of 1×10$^4$ cells/cm$^2$ in 75 cm$^2$ flasks containing M199 supplemented with 10% FBS, and incubated until the cultures contained well developed nodules (approximately 16 days). Conditioned media was precipitated by addition of ice-cold trichloroacetic acid to a final concentration of 15%. Precipitates were washed twice with 95% ethanol, dried, and resuspended in a buffer containing 62 mM Tris-Cl, pH 6.8, 1% SDS, 15% glycerol, 0.04% bromophenol blue, and 10% B-mercaptoethanol. Protein concentrations were established using a bicinchoninic acid assay (Pierce, Rockford, Ill.). After SDS-polyacrylamide gel electrophoresis proteins were electrophoretically transferred to nitrocellulose membranes (Schleicher & Schuell, Keene, N. H.) in buffer containing 192 mM glycine, 20% methanol, and 25 mM Tris-Cl, pH 8.3 and the resulting transfers incubated in a 5% dry milk solution at 37°, washed in Tris-buffered saline (TBS) containing 0.02% Tween 20, and incubated overnight at room temperature in the primary antibody (1:2000 dilution of anti-SGP2). After washing each transfer was incubated for 90 minutes at room temperature in a 1:200 dilution of horseradish peroxidase-conjugated donkey anti-rabbit antibody (Amersham Corporation, Arlington Heights, Ill.). Following extensive washing, immobilized antigens were visualized using an enhanced chemiluminescence assay (ECL: Amersham Corporation, Arlington Heights, Ill.) and exposed to X-ray film. Films were scanned and quantified by comparison with clusterin standards using a Metamorph Imaging System (Universal Imaging Corporation, West Chester, Pa.).

Northern Blots

Total cellular RNA was extracted from SMC cultures using Tri-Reagent (Molecular Research Center, Incorporated, Cincinnati, Ohio). Briefly, cultures were homogenized in Tri-Regent, phases were separated by addition of chloroform, and the upper aqueous phase was removed. RNA was precipitated with isopropanol, the pellet was washed with ethanol, and resuspended in Tris-EDTA buffer. Prior to electrophoresis in a 1% agarose gel, samples were denatured in 10% glyoxal and 50% formamide and heated to 65° for 10 min. Gels were then vacuum transferred in the presence of 22 mM NaOH to Genescreen Plus membranes (Dupont NEN, Boston, Mass. and neutralized. Nucleic acids were UV-crosslinked to the membrane (Stratalinker, Stratagene, La Jolla, Calif.) followed by pre-hybridization in 8% Denhardt's solution 43% formamide, 690 mM NaCl, 0.09% sodium pyrophosphate, 0.9% SDS, 0.7% dextran sulfate 1.74 mg/ml heparin and 86 µg/ml denatured salmon sperm DNA for >2 hours at 42° in a hybridization oven (Hybaid, Holbrook, N.Y.). Blots were hybridized overnight in the same solution by addition of a $^{32}$P-labeled cDNA probe. The membrane was washed twice at room temperature for 15 min. in 0.2% SDS and 1×SSC and once at 50° in 0.2% SDS and 0.1×SSC for 30 min. Radioactive signals were quantified using a Betagen Beta-scope (Intelligenetics Incorporated, Mountain View, Calif.) and autoradiograms were developed by exposure of blots X-ray film at −70° for 15–48 hours.

Total RNA was probed for smooth muscle α-actin using a full-length 1.3 kb mouse α-actin random-primer $^{32}$P labeled cDNA probe; for clusterin using a 1.2 kb random-primer $^{32}$P labeled cDNA fragment of porcine clusterin; for GAPDH using a 483 base pair random-primer $^{32}$P labeled PCR product from human GAPDH and for gp38k using a full-length random-primer $^{32}$P labeled cDNA encoding porcine gp38k.

Reverse Transcription and Polymerase Chain Reaction

RT-PCR was performed using total RNA from SM-CLU13AS and non-cloned smooth muscle cell cultures in order to determine if the antisense transcript was being expressed in G418 resistant clones. Total RNA (3ug in a final volume of 10 ul of water) was denatured for 5 min at 65° C., rapidly centrifuged, and quenched on ice for 2–3 min. Reverse transcription was performed in a buffer containing: 50 mM Tris-Cl, pH 8.3, 10 mM MgCl$_2$, 60 mM KCL, 10 mM dithiothreitol, 50 mg/ml oligo (dT) (Pharmacia, Upsala, Sweden), 0.5 mM dNTP mixture (U.S. Biochemical Corp., Cleveland, Ohio), 1 mg/ml bovine serum albumin, 1500 U/ml RNasin (Promega, Madison, Wis.), and 6000 U/Ml Superscript II M-MLV Reverse Transcriptase (Life Technologies, Gaithersburg, Md.). The reaction was incubated at 42° C. for 1 hr., followed by a 5 min incubation at 95° C., 20 ul of distilled water was added to the cDNA prior to PCR reactions.

In order to amplify cDNA from reverse transcription, polymerase chain reaction was performed in 50 ul samples containing 50 mM KCl, 10 mM Tris-HCl pH 8.3, 1.5 mM MgCl$^2$, 200 uM 4dNTP mixture, 1 uM each of the sense and antisense primers, 25 U/ml Taq DNA polymerase (Perkin Elmer, Branchburg, N.J.), and 5 ul of reverse transcribed cDNA as described above. Reactions were cycled 35 times as follows: 60 sec at 94°, 60 sec at 59°, and 150 sec at 72° in a Biometra UNOII thermocycler (Biometra, Inc., Tampa, Fla.). Murine clusterin primers (21 bp) were: ACATGTG-GAGTTCTGGTACGGG (SEQ ID NO. 12) (sense) and AGGAAGCCAAGAAGAAGAAAG (SEQ ID NO. 13) (antisense) and generate a product of 1221 base pairs. Porcine clusterin primers (21 bp) were: AAGCCAAGAA-GAAGAAAGAGG (SEQ ID NO. 14) (sense) and AGAT-AGTAGCGGTCGTCATTC (SEQ ID NO. 15) (antisense) and used as a positive control to generate a product of 922 bp.

Isolation and Characterization of Clusterin Negative Porcine VSMC Cell Line

To evaluate the role of clusterin in the formation of multicellular nodules, an antisense strategy was used to generate clusterin-negative stably transfected clones. VSMC clones were initially selected on the basis of G418 resistance and subsequently characterized by culture morphology and level of clusterin expression. This demonstrates for the first time that clusterin has a direct role in phenotypic modulation of cultured vascular smooth muscle cells and represents an essential mediator of that process.

Negative clones were selected from early passage cultures of porcine vascular smooth muscle cells co-transfected with two plasmids, pEMSV scribea2-CLU and pRSV neo, as described above. The pEMSV scribeα2-CLU contains the full length construct of murine clusterin in antisense orientation and pRSV neo contains the neomycin selectable marker. Following stable transfections 24 G418 resistant colonies were isolated and five clones were further evaluated. Clusterin expression was evaluated by western immunoassay of total secreted proteins in the G418 resistant clones and was diminished in two of the five clones (SM-CLU13AS and SM-CLU19AS) in comparison to noncloned SMC (lane NC) and to three other G418 resistant clones (SM-CLU15AS, SM-CLU18AS, and SM-CLU21AS). For this study we focused on a comparison of two of the G418 resistant clones, one which expresses very low level of clusterin, SM-CLU13AS, and one that expresses a relatively high level, SM-CLU18AS.

Northern blots were used to compare and evaluate clusterin mRNA expression in cloned and noncloned cultures. Although both clones express similar levels of the smooth muscle cell marker, SM α-actin, clone SM-CLU13AS expresses significantly less clusterin mRNA than does either SM-CLU19AS or noncloned cultures. This reduction in mRNA level is supported by western immunotransfer analysis of secreted proteins in which the level of clusterin expression is <1 ng/ug of total protein in SM-CLU13AS vs >20 ng/ug total protein in non cloned cultures as shown in Table 1.

TABLE 1

Clusterin expression in cloned and noncloned VSMC

| Cell Culture | Clusterin Expressed (ng clusterin/µg total protein) | Average |
|---|---|---|
| SM-CLU13AS | 1.3 | |
| | * | |
| | * | <1.3 |
| NC | 29.5 | |
| | 12.8 | |
| | 17.9 | 20.1 |

Samples of 24 hour conditioned medium from clone SM-CLU13AS and noncloned cells (NC) were collected and acid precipitated. Equal quantities of total secreted proteins were fractionated by gel electrophoresis and transferred to nitrocellulose membrane along with standard amounts of purified clusterin. After western analysis, the film was scanned and analyzed using Metamorph imaging software. The band intensities of the samples were compared with the band intensities of a standard curve generated from the purified clusterin samples. Results of three independently derived samples are presented as ng of clusterin/µg of total secreted protein. The clusterin signal in two of the SM-CLU13AS samples was below the level of sensitivity of the assay and is indicated by (*).

Morphology of SMC Clones

The morphology of SM-CLU13AS and SM-CLU18AS seeded into collagen-gels at identical cell densities and grown for 18 hr were evaluated. Comparison of the two panels demonstrated that SM-CLU13AS has not reorganized into nodules while the cells in SM-CLU18AS formed multicellular nodules. Non-cloned cultures also form nodules under these conditions.

Nodule Formation

Nodule formation typically requires a cell density of at least $4\times10^4$ cells/cm$^2$ and the presence of an extracellular gel on the substrate. The gel can be composed either of materials secreted and elaborated by the VSMC culture or provided exogenously as a Matrigel or collagen-gel substrate. Growth studies demonstrate that the population doubling time is virtually identical for SM-CLU13AS and SM-CLU18AS establishing that the required cell density is achieved by each clone (data not presented). Additionally, each culture was incubated for up to 23 days and even after that amount of time SM-CLU13AS failed to form nodules. Clearly the lack of nodules is not simply a failure to proliferate or insufficient time in culture.

Further, SM-CLU13AS were seeded onto preformed collagen-gel or Matrigel substrates; conditions previously shown to facilitate nodule formation by clusterin-positive VSMC. SM-CLU13AS do not form nodules when seeded onto collagen-gel, but do form nodules when seeded onto clusterin-containing Matrigel. In comparison, SM-CLU18AS forms nodules on either substrate (Table2). Matrigel contains relatively high levels of clusterin while clusterin is not detectable in the collagen-gel.

TABLE 2

| Conditioned Medium | Substrate | Nodule Density (Nodule/4 mm$^2$) |
|---|---|---|
| None (Control) | collagen-gel | 0 |
| NCM | collagen-gel | 21 |
| NCM | collagen-gel | 25 |
| SM-CLU18AS-CM | collagen-gel | 25 |
| SM-CLU18AS-CM | collagen-gel | 26 |
| SM-CLU18AS-CM + Ab | collagen-gel | 5 |
| SM-CLU18AS-CM + Ab | collagen-gel | 6 |

Conditioned media prepared from noncloned VSMC (NCM) and clone SM-CLU18AS cells were collected and concentrated as described. Clone SM-CLU 13AS cells were seeded, as described, on collagen-gel substrates. Cells were cultured for 12 hour in the absence (control) or presence of clusterin-conditioned media (NCM or SM-CLU18AS-CM) supplemented M199+10% FBS. The addition of 4 µl anti-clusterin polyclonal antibody is indicated by (+Ab). Nodule density was evaluated using Metamorph software.

The effect on nodule formation of nodular cell culture conditioned medium which contains clusterin was tested. SM-CLU13AS forms nodules in the presence of SMC clusterin presented in conditioned media. To establish that the SM-CLU18AS-conditioned medium effect was due to clusterin we incubated the medium with anti-clusterin antibody before addition to the cell culture. The number of nodules was reduced approximately 80% from 26/4 mm$^2$ to 5/4 mm2. Therefore we concluded that the failure to form nodules in clone SM-CLU13AS does not result from an intrinsic inability to form nodules, but results from the absence of endogenous or exogenous clusterin.

RT-PCR was used to determine if clone SM-CLU13AS expressed murine antisense RNA Total RNA from clone SM-CLU13AS and from noncloned cells was reverse transcribed, as described above, and incubated with 21 bp primers designed to generate a PCR product of 1221 bp. A 1221 bp product was detected in the SM-CLU13AS reaction but not in RNA from noncloned VSMC. Primers to porcine clusterin were designed to generate a product of 922 bp which was detected in both the SM-CLU13AS and non-cloned RNA preparations. Clearly, the antisense construct is being expressed in clone SM-CLU13AS.

In contrast to monolayer cell cultures, nodular VSMC express markers of smooth muscle cell differentiation and synthesize and secrete relatively high levels of clusterin. Further, nodule formation is accelerated after the addition of cell culture conditioned medium from nodular cell cultures (NCM). This can be demonstrated by seeding VSMC on a gelatinous matrix composed of Matrigel, or by seeding VSMC onto a collagen-gel matrix. A gelatinous matrix, such as Matrigel, in which clusterin is already present as a constituent, provides an environment analogous to the vascular wall into which the VSMC invade and differentiate.

A plasmid-mediated antisense RNA strategy was used to transfect early passage culture of porcine VSMC with pEMSV scribe α2 containing full-length murine clusterin in antisense orientation. Transfected clones were shown by RT-PCR analysis to express the murine sequence. Some of the G418-selected clones continued to express clusterin. These clones were used to compare the nodule forming activity of VSMC clones expressing either high and low levels of clusterin.

SM-CLU13AS expresses low levels of clusterin and fails to form nodules even after 23 days in culture. However, SM-CLU13AS retains the capacity to nodulate in response to the addition of clusterin-containing Matrigel. SM-CLU13AS is defective in clusterin expression and retains the ability to form nodules only when exogenous clusterin is provided.

Adhesion To Collagen-gels

A peptide representing clusterin amino acids 118–132, having the sequence K-Q-T-C-M-K-F-Y-A-R-V-C-R-S-G (SEQ ID NO. 11), blocks the adhesion of SM-CLU13AS cells to gelatin. Two other synthetic peptides whose sequences are based on other regions of the clusterin sequence were without detectable effects. Exposure to a scrambled version of the 118–132 peptide, having the sequence S-Y-R-R-C-A-M-Q-G-F-K-V-K-T-C (SEQ ID NO. 16) which was prepared, purified, and presented exactly as was 118–132 did not affect adhesion to the substrate.

Antibody Neutralization of the Clusterin Effect

To demonstrate the ability of anti-clusterin antibodies to inhibit nodule formation, collagen gel cultures were treated with anti-clusterin antibodies to block clusterin's activity. Collagen gel solutions were supplemented with anti-clusterin antibody (10 µg antibody/400 µl gel solution) and used to coat each well of a 6-well cluster dish. Additionally, 2.5 µg antibody was added to the cells just before they were added to the wells containing the gel. Control samples contained 12.5 µg of antibody which was preincubated with 4 µg of purified plasma clusterin at room temperature for one hour prior to mixing with the collagen gel solution. After 24 hours on collagen gel the culture had formed well developed multilayered ridges but not the nodules that were formed in 24 hours by cultures on Matrigel. Nodules did form in collagen gel cultures after 72 hours of incubation. After 24 hours the culture had formed well developed multilayered ridges and by 72 hours a well developed nodule was evident. In contrast, cultures grown in collagen gel supplemented with anti-clusterin are shown at 24 and 72 hours. In the presence of antibody the multilayered ridge was less well developed after 24 hours and nodules had not formed by 72 hours. After 72 hours in the presence of anti-clusterin, the culture showed ridge formation similar to that seen in the untreated cultures at 24 hours.

Cell Migration Assay

Migration assays were conducted in a 48 well microchemotaxis chamber containing PVP-free polycarbonate membranes with 12 µm pores (Neuro Probe Inc., Cabin John, Md.) coated with a 0.1 mg/ml solution of collagen IV (Trevigen, Gaithersburg, Md.) and dried. The bottom chamber contained RPMI plus 0.1% BSA and 0.001–10 µg/well of clusterin. The positive control chambers contained 10 ng/ml PDGF. RPMI plus 0.1% BSA was used as the negative control. 50,000 cells per well were added to the upper chamber and after incubation at 37° C. for four hours, the filters were fixed and stained using Diff-Quik (Baxter Healthcare Corporation, McGraw Park, Ill.). In some experiments clusterin was mixed with anti-sgp-2 antibody at concentrations of 1:50 or 1:100 for ten minutes before addition to the lower chamber. Cells that migrated through the filter was quantitated by counting the center of each well at 10× using an Olympus CK2 microscope. Each condition was assayed in triplicate wells and each experiment was repeated three times. Clusterin was maximally active at 0 µg.

Gp38k

The structure of gp38k was initially reported in 1985 but its function has been unknown. We have found that gp38k, at concentrations as low as 1 ng/ml, is as effective in promoting HUVEC migration as is 5 ng/ml bFGF. The number of cells migrating in response to gp38k is increased by a statistically significant 100%. Further, the gp38k mediated migration is virtually eliminated after incubation with an affinity purified polyclonal anti-gp38k antibody. To determine if gp38k modulates endothelial cell morphology, a well established in vitro model of capillary tube morphogenesis, the Matrigel invasion assay was utilized. Gp38k promoted the formation of branching tubules in this assay system, although concentrations greater than those required for cell migration were required. The basis for the difference in concentrations remains to be established. However, it may be due to the greater amount of time required for the tube forming assay or to binding of gp38k in to the Matrigel substrate. Gp38k is bound by heparin and may be sequestered by heparin-like glycosaminoglycans in the Matrigel. Alternatively, the active concentrations of gp38k required for the very different processes of migration and differentiation may vary greatly. These observations are not unlike those described for the peptide growth factors PDGF and TGFβ.

Cell Culture

HUVECs were isolated from freshly delivered umbilical cords and grown as previously reported. For migration assays, cells were harvested using Versene (Life Technologies, Gaithersburg, Md.) and resuspended in RPMI 1640 containing 0.1% BSA.

Gp38k Purification

Gp38k was purified from nodular VSMC serum-free conditioned medium prepared by washing cultures three times with HBSS before incubation for 16–24 hours in serum free M199. The medium was collected into 1 nM phenyl-methyl sulfonyl fluoride in 100% ethanol (PMSF; Sigma, St. Louis, Mo.) and 1% aprotinin (Trasylol; Meloy Labs, NY); centrifuged for 15 minutes at room temperature at 10,000 rpm, and stored at −20° C.

Conditioned medium (300 ml) was fractionated by passage through a 10 ml gelatin-Sepharose 4B (Pharmacia, Piscataway, N.J.) column. The gelatin-nonbound fraction was then passed through a 5 ml heparin-Sepharose (Pharmacia) column and the column washed with phosphate buffered saline containing 0.02% sodium azide. The heparin-bound material was eluted sequentially with 20 mM Tris-HCl, pH=7.4, containing either 300 mM. 400 mM, and finally 1 M NaCl. Eluted fractions were concentrated in an Centriprep-30 spin concentrator (Amicon, Beverly, Mass.) and examined using silver stained SDS-polyacrylamide gels. Fractions containing gp38k were pooled and size fractionated with a Pharmacia FPLC using a 1.6×60 cm Superdex 75 prepgrade column running at 1.5 ml/min. Recovered fractions were concentrated in an Centriprep-30 spin concentrator and examined in silver stained SDS-polyacrylamide gels.

Cell Migration Assay

Migration assays were conducted in a 48 well microchemotaxis chamber containing PVP-free polycarbonate membranes with 12 µm pores (Neuro Probe Inc., Cabin John, Md.) coated with a 0.1 mg/ml solution of collagen IV (Trevigen, Gaithersburg, Md.) and dried. The bottom chamber contained RPMI plus 0.1% BSA and 0.15–1000 ng/ml of gp38k. The positive control chambers contained 5 ng/ml bFGF. RPMI plus 0.1% BSA was used as the negative control. 50,000 cells per well were added to the upper chamber and after incubation at 37° C. for four hours, the filters were fixed and stained using Diff-Quik (Baxter Healthcare Corporation, Mc Graw Park, Ill.). In some experiments gp38k was mixed with anti-gp38k antibody at concentrations of 1:50 or 1:100 for ten minutes before addition to the lower chamber. Cells that migrated through the filter were quantitated by counting the center of each well at 10× using an Olympus CK2 microscope. Each condition was assayed in triplicate wells and each experiment was repeated three times.

Checkerboard Assay

Chemotaxis/chemokinesis assays were performed using conditions described above for cell migration assays with the exception that the upper chamber was also supplemented with various concentrations of gp38k protein. Each condition was assayed in triplicate wells and each experiment was repeated at least three times.

HUVEC Tube Forming Assays

Tube forming assays were performed on 48-well plates that had been coated with 200 µl of Matrigel per well. Cells from confluent HUVEC cultures were detached with 0.05% trypsin (Life Technologies, Gaithersburg, Md.), 0.53 mM ethylenediamine tetraacetic acid (EDTA) in Hanks' Balanced Salt Solution. Cells were plated at a density of 24,000 cells/well in 250 µl of HUVEC media containing 5% Bovine Calf Serum. Samples of gp38k were tested at concentrations of 100–1000 ng/ml, as indicated. Tubes were allowed to form by incubating overnight at 37° C. before adding Diff-Quick solutions to fix and stain cells. Assays were done in triplicate three times.

Polyclonal Antibody Preparation

Polyclonal anti-gp38k antibodies were prepared by multiple immunizations of White New Zealand male rabbits using gp38k, purified as described above, in Freunds adjuvant. Antiserum was titered by Western immunoassay and the IgG fraction purified using an Econo-Pac Serum IgG Purification Kit (Bio-Rad, Hercules, Calif.) following the manufacturer's instructions. Antibodies were then affinity purified by adsorption to gp38k on Immobilon-NC membranes (Millipore, Bedford, Mass.). Antibody was eluted from the membrane in a buffer composed of 100 mM glycine, 0.5 MNaCl, and 0.05% Tween 20 at pH=2.3 and immediately neutralized with 1 M $Na_2HPO_4$ at pH=9.0. Affinity purified antibodies were tested and titered using western immunoassays.

Statistics

In Stat software was used to calculate statistical significance using the Welch's t-test.

Cell Migration

The effect of gp38k on HUVEC migration was tested in Boyden chambers using collagen IV-coated membranes. Cells were added to the upper chamber and after 4 hours the number of cells migrating through the membrane in response to gp38k in the lower chamber was quantified. Cell migration was significantly increased 2 fold (P<0.0001) over migration in response to BSA supplemented media alone. The effect was dose-dependent and reached a maximal level similar to that produced in response to the control chemoattractant bFGF. Maximal migration was achieved at 1 ng/ml gp38k and migration diminished at higher concentrations. To evaluate the specificity of the gp38k response, HUVEC migration was evaluated in the presence of gp38k incubated with affinity purified anti-gp38k antibody. The migratory response to gp38k is eliminated in the presence of either a 1:50 or 1:100 dilution of polyclonal anti-gp38k and HUVEC migration is reduced to the basal level observed in the control wells.

The effect of gp38k on VSMC migration was tested as well. Dose response studies demonstrated that gp38k was again maximally active at 1 ng/ml. VSMC migration was significantly increased 15× over control and greater than 10× over migration in response to the known chemoattractant, PDGF. Importantly and significantly, the migration response was eliminated in the presence of anti-gp38k antibody. Gp38k-mediated migration was also evaluated using non vascular cells (human fibroblasts) with minimal response. The response was equal to that of the background activity (M199+0.1% BSA) although fibroblasts did respond to PDGF with a 3.5× increase in migration.

Gp38k Promotes Directional Migration

Checkerboard assays were performed to determine if gp38k acts via chemoattraction (directional migration) or chemokinesis (random motility). Concentrations of gp38k, ranging from 0.25 to 10 ng/ml were present in the top and bottom compartments of the Boyden chamber apparatus. The greatest number of cells was found to be migrating along the chemotactic gradient, in response to 1 ng/ml gp38k. No significant stimulation of migration was observed when gp38k was in either the upper chamber or in both chambers indicating that this protein has no effect on random motility. These results indicate that gp38k functions as a chemoattractant to stimulate directional migration of HUVEC.

Tube Formation

When endothelial cells are plated on a Matrigel substrate they attach, migrate, and form tubular structures. The effect of gp38k was tested in this in vitro model system of endothelial cell differentiation. Cells were seeded on Matrigel substrates in the presence or absence of added gp38k. Gp38k enhanced tube formation at 100 ng/ml relative to cultures in non-supplemented Matrigel. This process of cell organization and branching involves cell motility and is further evidence of gp38k activity with endothelial cells.

By sequence homology, gp38k could be categorized as a member of the glycosyl hydrolase family of 18 enzymes and proteins which include chitinases. However, it is unlikely that gp38k functions as a glycosyl hydrolase.

Hybridomas and Monoclonal Antibodies

Monoclonal antibody to gp38k protein or clusterin are prepared by immunizing a Balb/c mouse (Jackson Laboratories, Bar Harbor, Me.) with 100 µg of partially purified gp38k protein or clusterin in Freund's complete adjuvant (Gibco, Grand Island, N.Y.). The mouse is boosted with 50 µg of protein in Freund's incomplete adjuvant 4 and 6 weeks later. Three days after the last injection, mouse spleen cells are collected and fused with NS-1 myeloma cells (Koehler and Milstein, 1975). Hybridomas are screened by means of an ELISA using 96-well plates coated with 0.6–1 µg/well of partially purified gp38k or clusterin. The positive clones are further screened and finally used for the production of ascitic fluid. IgG fractions are purified from the ascitic fluid using diethylaminoethyl (DEAE)-cellulose column chromatography. Specificity of the antibody is established using Western transfer analysis and immunoprecipitation.

Peptides

Proteins are organized into discrete independently folded domains that reflect functional segregation within the molecule. Gp38k (SEQ ID NO. 17) is a single polypeptide, has only one n-linked glycosylation site, and is active in promoting cell migration at very low concentrations. As described above, clusterin is an 80 kDA heterodimeric glycoprotein.

Identification, isolation and characterization of the active domains of clusterin and gp38k is conducted as follows. Proteolytic fragments are obtained by limited proteolysis followed by affinity chromatography and then tested in the cell migration assay. Additionally, peptides may be chemically synthesized or cloned into fusion protein constructs for expression. The following peptides may be used to alter cell migration:

Clusterin Peptides

1. L-W-E-E-C-K-P-C-L-K-Q-T-C (SEQ ID NO. 8)
2. L-M-E-N-D-R-Q-Q-S-H-V-M-D-I-M-E-D (SEQ ID NO. 9
3. K-Q-L-N-E-Q-F-S-W-V-S-Q-L-A (SEQ ID NO. 10)
4. D-K-A-I-S-D-K-E-L-Q-E-M-S-T-E-G-S-K-Y-V (SEQ ID NO. 7)
5. K-Q-T-C-M-K-F-Y-A-R-V-C-R-S-G (SEQ ID NO. 11)

gp38k Peptides

1. T-L-L-S-V-G-G-W-N-F-G-S-Q-R (SEQ ID NO. 1)
2. R-T-H-G-F-D-G-L-D-L-A (SEQ ID NO. 2)
3. P-G-R-R-D-R-R-H-L-T-T-L-V-K-E-M (SEQ ID NO. 3)
4. V-A-I-D-R-G-Y-D-I-A-Q-I-S-Q-H-L-D-F-I (SEQ ID NO. 4)
5. F-G-R-S-F-T-L-A-S-S-K-T-D (SEQ ID NO. 5)
6. N-L-R-F-P-L-T-S-A-I-K-D (SEQ ID NO. 6)

Chimeric Antibodies against Clusterin and gp38k

Human-mouse chimeric antibodies are produced as follows: mRNA is isolated from a mouse hybridoma cell line producing the mAb, cloned, and cDNA produced therefrom. A full-length cDNA library from purified mRNA is prepared from which the appropriate V region gene segments of the L and H chain genes can be identified with appropriate probes, sequenced, and made compatible with a C gene segment. C region gene segment modules are prepared by cDNA preparation and cloning. Complete H or L chain-coding sequences are constructed by linkage of the cloned specific immunoglobulin V region segments described above to cloned human C region gene segment modules. Finally, chimeric L and H chains are expressed in selected prokaryotic and eucaryotic host cells.

Expression vehicles include plasmids or other vectors. Preferred among these are vehicles carrying a functionally complete human C heavy or C light chain sequence having appropriate restriction sites engineered so that anu variable H or variable L shcin sequence with appropriate cohesive ends can be easily inserted thereinto. Human C heavy or C light chain sequence-containing vehicles are thus an important embodiment of the invention. These vehicles can be used as intermediates for the expression of any desired complete H or L chain in any appropriate host.

One preferred host is yeast. Because yeast cells carry out post-translational peptide modifications including glycosylation, yeast provides substantial advantages for the production of immunoglobulin L and H chains. A number of recombinant DNA strategies now exist which utilize strong promoter sequences and high copy number plasmids which can be used for production of the desired proteins in yeast.

Anti-sense Nucleotides

Synthetic oligonucleotides which code for RNAs that are complementary to and capable of binding to transcribed sequences of gp38k and clusterin are effective in inhibiting expression and translation of gp38k and clusterin. The anti-sense nucleotides are applied directly to the desired locus of the cells to be treated, where they hybridize with the mRNA and inhibit the activity of the protein which would result from translation of the mRNA. Devices for localized anti-sense application and methods are described elsewhere, e.g. U.S. Pat. No. 5,593,974, the contents of which are incorporated by reference into the subject application in their entirety.

Inhibition or Enhancement of Angiogenesis

New capillaries are formed wherever there is a need for them. When cells in tissues are deprived of oxygen angiogenic factors are released to induce new capillary growth. Use of migration-altering compositions of the present invention to enhance migration can be used to initiate the process by which new blood vessels are formed. For example, in the event that blockage of a blood vessel has occurred due to coronary artery disease and surgical bypass or similar intervention is contraindicated, a therapeutically effective amount of a migration-altering composition such as clusterin, or gp38k alone or in combination is administered directly to the site of the blockage to facilitate the development of new blood vessels to circumvent the blockage.

Angiogenesis is also important in tumor growth. The growth of a solid tumor is limited by its blood supply and a tumor must induce the formation of a capillary network that invades the tumor mass to continue growing. Migration-altering compositions which inhibit clusterin and gp38k related functions, for example, antisense polynucleotides derived from the sequence of clusterin and gp38k, or antibodies directed against clusterin and gp38k proteins and related peptides, are useful as anti-tumor agents.

In accordance with the methods of the present invention, the migration-altering compositions of the invention can be administered by means known to those of skill in the art. For example, percutaneous transluminal coronary angioplasty (PTCA) balloon dilation catheters (U.S. Pat. Nos. 5,102,402 and 5,199,951) have been designed with coatings of drugs on the external surface of the balloon. Other PTCA catheters contain perforations in the wall of the PTCA balloon for infusion of drugs such as the Wolinsky catheter or the balloon within a balloon design seen in U.S. Pat. No. 5,049,132. Other catheters such as the Stack perfusion catheter and the catheter embodied in U.S. Pat. No. 5,181,971 were designed to facilitate drug delivery without disrupting distal tissue perfusion. The drug delivery device of U.S. Pat. No. 5,985,307 provides a means for local delivery of a therapeutic agent directly into the boundary layer of blood flowing through a predetermined site within a blood vessel.

Gp38k, a protein expressed by VSMC and other cell types during periods of tissue remodeling is functionally active in promoting HUVEC migration and tubulogenesis. These results indicate, for the first time, that gp38k functions as a chemoattractant, in vitro, and raises the possibility that it may have a similar effect during vascular remodeling or other processes associated with restenosis, in vitro. Migration-altering compositions in accordance with the present invention can be used to modulate cell migration during tissue remodeling in the vascular wall during pathologic arterial restructuring.

While the invention has been described with reference to preferred embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method of altering cell migration by contacting cells with a migration-altering composition wherein said migration-altering composition is an antibody to gp38k (SEQ ID NO 17).

2. The method of claim 1, wherein said migration-altering composition is an antibody which inhibits the chemotactic activity of gp38k (SEQ ID NO 17).

3. The method of claim 1, wherein said antibody is selected from the group consisting of antibodies to gp38k (SEQ ID NO 17), antibodies to gp38k fragments, antibodies to gp38k peptides and a combination thereof.

* * * * *

```
                            SEQUENCE LISTING

<160> NUMBER OF SEQ ID NOS: 17

<210> SEQ ID NO 1
<211> LENGTH: 14
<212> TYPE: PRT
<213> ORGANISM: Artificial Sequence
<220> FEATURE:
<223> OTHER INFORMATION: Description of Artificial Sequence:SITE
<221> NAME/KEY: SITE
<222> LOCATION: (1)..(14)
<223> OTHER INFORMATION: peptide corresponding to amino acids 92-105 of
      gp38k protein

<400> SEQUENCE: 1

Thr Leu Leu Ser Val Gly Gly Trp Asn Phe Gly Ser Gln Arg
  1               5                  10

<210> SEQ ID NO 2
<211> LENGTH: 11
<212> TYPE: PRT
<213> ORGANISM: Artificial Sequence
<220> FEATURE:
<223> OTHER INFORMATION: Description of Artificial Sequence:SITE
<221> NAME/KEY: SITE
<222> LOCATION: (1)..(11)
<223> OTHER INFORMATION: peptide corresponding to amino acids 128-138 of
      gp38k protein

<400> SEQUENCE: 2

Arg Thr His Gly Phe Asp Gly Leu Asp Leu Ala
  1               5                  10

<210> SEQ ID NO 3
<211> LENGTH: 16
<212> TYPE: PRT
<213> ORGANISM: Artificial Sequence
<220> FEATURE:
<223> OTHER INFORMATION: Description of Artificial Sequence:SITE
<221> NAME/KEY: SITE
<222> LOCATION: (1)..(16)
<223> OTHER INFORMATION: peptide corresponding to amino acids 142-157 of
      gp38k protein

<400> SEQUENCE: 3

Pro Gly Arg Arg Asp Arg Arg His Leu Thr Thr Leu Val Lys Glu Met
  1               5                  10                  15

<210> SEQ ID NO 4
<211> LENGTH: 19
<212> TYPE: PRT
<213> ORGANISM: Artificial Sequence
<220> FEATURE:
<223> OTHER INFORMATION: Description of Artificial Sequence:SITE
<221> NAME/KEY: SITE
<222> LOCATION: (1)..(19)
```

```
<223> OTHER INFORMATION: Peptide corresponding to amino acids 183-201 of
      gp38k protein

<400> SEQUENCE: 4

Val Ala Ile Asp Arg Gly Tyr Asp Ile Ala Gln Ile Ser Gln His Leu
 1               5                  10                  15

Asp Phe Ile

<210> SEQ ID NO 5
<211> LENGTH: 13
<212> TYPE: PRT
<213> ORGANISM: Artificial Sequence
<220> FEATURE:
<223> OTHER INFORMATION: Description of Artificial Sequence:SITE
<221> NAME/KEY: SITE
<222> LOCATION: (1)..(13)
<223> OTHER INFORMATION: Peptide corresponding to amino acids 261- 273
      of gp38k protein

<400> SEQUENCE: 5

Phe Gly Arg Ser Phe Thr Leu Ala Ser Ser Lys Thr Asp
 1               5                  10

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence:SITE
<221> NAME/KEY: SITE
<222> LOCATION: (1)..(12)
<223> OTHER INFORMATION: Peptide corresponding to amino acids 367-378 of
      gp38k protein

<400> SEQUENCE: 6

Asn Leu Arg Phe Pro Leu Thr Ser Ala Ile Lys Asp
 1               5                  10

<210> SEQ ID NO 7
<211> LENGTH: 20
<212> TYPE: PRT
<213> ORGANISM: Artificial Sequence
<220> FEATURE:
<223> OTHER INFORMATION: Description of Artificial Sequence:SITE
<221> NAME/KEY: SITE
<222> LOCATION: (1)..(20)
<223> OTHER INFORMATION: Peptide corresponding to amino acids 23-42 of
      porcine clusterin

<400> SEQUENCE: 7

Asp Lys Ala Ile Ser Asp Lys Glu Leu Gln Glu Met Ser Thr Glu Gly
 1               5                  10                  15

Ser Lys Tyr Val
            20

<210> SEQ ID NO 8
<211> LENGTH: 13
<212> TYPE: PRT
<213> ORGANISM: Artificial Sequence
<220> FEATURE:
<223> OTHER INFORMATION: Description of Artificial Sequence:SITE
<221> NAME/KEY: SITE
<222> LOCATION: (1)..(13)
<223> OTHER INFORMATION: Peptide corresponding to amino acids 109-121 of
      porcine clusterin

<400> SEQUENCE: 8

Leu Trp Glu Glu Cys Lys Pro Cys Leu Lys Gln Thr Cys
```

```
<210> SEQ ID NO 9
<211> LENGTH: 17
<212> TYPE: PRT
<213> ORGANISM: Artificial Sequence
<220> FEATURE:
<223> OTHER INFORMATION: Description of Artificial Sequence:SITE
<221> NAME/KEY: SITE
<222> LOCATION: (1)..(17)
<223> OTHER INFORMATION: Peptide corresponding to amino acids 162-178 of
      porcine clusterin

<400> SEQUENCE: 9

Leu Met Glu Asn Asp Arg Gln Gln Ser His Val Met Asp Ile Met Glu
 1               5                  10                  15

Asp

<210> SEQ ID NO 10
<211> LENGTH: 14
<212> TYPE: PRT
<213> ORGANISM: Artificial Sequence
<220> FEATURE:
<223> OTHER INFORMATION: Description of Artificial Sequence:SITE
<221> NAME/KEY: SITE
<222> LOCATION: (1)..(14)
<223> OTHER INFORMATION: Peptide corresponding to amino acids 359-372 of
      porcine clusterin

<400> SEQUENCE: 10

Lys Gln Leu Asn Glu Gln Phe Ser Trp Val Ser Gln Leu Ala
 1               5                  10

<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence:SITE
<221> NAME/KEY: SITE
<222> LOCATION: (1)..(15)
<223> OTHER INFORMATION: Peptide corresponding to amino acids 118-132 of
      porcine clusterin

<400> SEQUENCE: 11

Lys Gln Thr Cys Met Lys Phe Tyr Ala Arg Val Cys Arg Ser Gly
 1               5                  10                  15

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence:primer_bind
<223> OTHER INFORMATION: synthetic sense primer based on murine
      clusterin

<400> SEQUENCE: 12
acatgtggag ttctggtacg gg                                          22

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence:primer_bind
<223> OTHER INFORMATION: synthetic antisense primer based on murine
      clusterin
```

```
<400> SEQUENCE: 13
aggaagccaa gaagaagaaa g                                               21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence:primer_bind
<223> OTHER INFORMATION: synthetic sense primer based on porcine
      clusterin

<400> SEQUENCE: 14
aagccaagaa gaagaaagag g                                               21

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence:primer_bind
<223> OTHER INFORMATION: synthetic antisense primer based on porcine
      clusterin

<400> SEQUENCE: 15
agatagtagc ggtcgtcatt c                                               21

<210> SEQ ID NO 16
<211> LENGTH: 15
<212> TYPE: PRT
<213> ORGANISM: Artificial Sequence
<220> FEATURE:
<223> OTHER INFORMATION: Description of Artificial Sequence:mutagen
<221> NAME/KEY: MUTAGEN
<222> LOCATION: (1)..(15)
<223> OTHER INFORMATION: Peptide representing scrambled version of amino
      acids 118-132 of porcine clusterin

<400> SEQUENCE: 16
```

Ser Tyr Arg Arg Cys Ala Met Gln Gly Phe Lys Val Lys Thr Cys
 1               5                  10                  15

```
<210> SEQ ID NO 17
<211> LENGTH: 383
<212> TYPE: PRT
<213> ORGANISM: Sus scrofa

<400> SEQUENCE: 17
```

Met Gly Leu Arg Val Ala Gln Thr Gly Phe Val Ala Leu Val Leu Leu
 1               5                  10                  15

Gln Ser Cys Ala Ala Tyr Lys Leu Val Cys Tyr Tyr Thr Ser Trp Ser
                20                  25                  30

Gln Tyr Arg Glu Gly Asp Gly Ser Cys Phe Pro Asp Ala Ile Asp Pro
            35                  40                  45

Phe Leu Cys Thr His Ile Ile Tyr Ser Phe Ala Asn Ile Ser Asn Asn
        50                  55                  60

Glu Ile Asp Thr Leu Glu Trp Asn Asp Val Thr Leu Tyr Asp Thr Leu
65                  70                  75                  80

Asn Thr Leu Lys Asn Arg Asn Pro Asn Leu Lys Thr Leu Leu Ser Val
                85                  90                  95

Gly Gly Trp Asn Phe Gly Ser Gln Arg Phe Ser Lys Ile Ala Ser Asn
            100                 105                 110

Thr Gln Ser Arg Arg Thr Phe Ile Lys Ser Val Pro Pro Phe Leu Arg

-continued

```
            115                 120                 125
Thr His Gly Phe Asp Gly Leu Asp Leu Ala Trp Ile Ser Pro Gly Arg
    130                 135                 140

Arg Asp Lys Arg His Leu Thr Thr Leu Val Lys Glu Met Lys Ala Glu
145                 150                 155                 160

Phe Val Arg Glu Ala Leu Pro Gly Thr Glu Arg Leu Leu Leu Ser Gly
                165                 170                 175

Ala Val Ser Ala Gly Lys Val Ala Ile Asp Arg Gly Tyr Asp Ile Ala
                180                 185                 190

Gln Ile Ser Gln His Leu Asp Phe Ile Ser Leu Leu Thr Tyr Asp Phe
                195                 200                 205

His Gly Ala Trp Arg Gln Thr Thr Gly His His Ser Pro Leu Phe Arg
    210                 215                 220

Gly Gln Gly Asp Ala Ser Ser Asp Arg Phe Ser Asn Ala Asp Tyr Ala
225                 230                 235                 240

Val Ser Tyr Val Leu Arg Leu Gly Ala Pro Ala Asn Lys Leu Val Met
                245                 250                 255

Gly Ile Pro Thr Phe Gly Arg Ser Phe Thr Leu Ala Ser Ser Lys Thr
                260                 265                 270

Asp Val Gly Ala Pro Ala Ser Gly Pro Gly Ile Pro Gly Arg Phe Thr
                275                 280                 285

Lys Glu Lys Gly Ile Leu Ala Tyr Tyr Glu Ile Cys Asp Phe Leu Gln
    290                 295                 300

Gly Ala Thr Val Arg Arg Pro Leu Gly Gln Gln Val Pro Tyr Ala Thr
305                 310                 315                 320

Lys Gly Asn Gln Trp Val Gly Tyr Asp Asp Gln Glu Ser Val Lys Asn
                325                 330                 335

Lys Ala Lys Tyr Leu Lys Ser Arg Gln Leu Ala Gly Ala Met Val Trp
                340                 345                 350

Thr Leu Asp Leu Asp Asp Phe Arg Gly Asn Phe Cys Gly Gln Asn Leu
    355                 360                 365

Arg Phe Pro Leu Thr Ser Ala Ile Lys Asp Val Leu Ala Ala Ala
    370                 375                 380
```